(12) United States Patent
Johs et al.

(10) Patent No.: US 7,167,241 B1
(45) Date of Patent: Jan. 23, 2007

(54) DIELECTRIC FUNCTION OF THIN METAL FILMS DETERMINED BY COMBINED TRANSMISSION SPECTROSCOPIC ELLIPSOMETRY AND INTENSITY MEASUREMENTS

(75) Inventors: Blaine D. Johs, Lincoln, NE (US); Gregory K. Pribil, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 424 days.

(21) Appl. No.: 10/884,718

(22) Filed: Jul. 4, 2004

Related U.S. Application Data

(60) Provisional application No. 60/485,007, filed on Jul. 5, 2003.

(51) Int. Cl.
*G01J 4/00* (2006.01)
*G01B 11/06* (2006.01)

(52) U.S. Cl. .................. 356/364; 356/369; 356/630
(58) Field of Classification Search ........ 356/364–369, 356/630–632, 445; 702/170, 65, 66, 75; 703/2
See application file for complete search history.

(56) References Cited

U.S. PATENT DOCUMENTS

| | | | |
|---|---|---|---|
| 5,403,433 A * | 4/1995 | Morrison et al. | 216/60 |
| 5,706,212 A * | 1/1998 | Thompson et al. | 702/85 |
| 5,796,983 A * | 8/1998 | Herzinger et al. | 703/2 |
| 5,835,221 A * | 11/1998 | Lee et al. | 356/369 |
| 5,900,633 A * | 5/1999 | Solomon et al. | 250/339.08 |
| 6,034,777 A | 3/2000 | Johs et al. | 356/369 |
| 6,353,477 B1 | 3/2002 | Johs et al. | 356/369 |
| 6,456,376 B1 | 9/2002 | Liphardt et al. | 356/369 |
| 6,862,095 B2 * | 3/2005 | Horie | 356/445 |
| 7,110,912 B1 * | 9/2006 | Tiwald | 702/170 |
| 2005/0179897 A1* | 8/2005 | Synowicki et al. | 356/369 |

OTHER PUBLICATIONS

McGahan et al., Thin Solid Films 234 (1993).
An et al, Rev. Sci. Instrum. 65 (1994).
H. Arwin and D. E. Aspnes, Thin Solid Films 113 (1984) 101.
H.V. Nguyen, Ilsin An, and R.W. Collins, Phys. Rev. Lett. 68 (1992) 994.
H.V. Nugyen, Ilsin An, and R.W. Collins, Phys. Rev. B 47 (1993) 3947.
M2000XI, J.A. Woollam Co., Inc., Lincoln, NE.
B. Johs, J. Hale, N.J. Ianno, C.M. Herzinger, T. Tiwald, and J.A. Woollam, Proc. SPIE 4449 (2001) 41.
R. Kleim, L. Kuntzler, and A. El Ghemmaz, J. Opt. Soc. Am. A 11 (1994) 2550.
P.I. Rovira and R.W. Collins, J. Appl. Phys. 85 (1999) 2015.
Johs, French, Kalk, McGahan and Woollam, SPIE vol. 2253, (1994).
R. Joerger, K. Forcht, A, Gombert, M. Khl, and W. Graf, Appl. Opt. 36 (1997) 319.

(Continued)

*Primary Examiner*—Hoa Q. Pham
(74) *Attorney, Agent, or Firm*—James D. Welch

(57) ABSTRACT

Determination of thin metal film dielectric function and layer thicknesses using simultaneous transmission spectroscopic ellipsometric (SE) and transmission intensity (T) measurements obtained in-situ to break correlation between thickness and optical constants of very thin absorbing films, preferably using only A.C. Components of ellipsometric and intensity characterizing electromagnetic radiation which transmits through said substrate and enters a detector.

15 Claims, 11 Drawing Sheets

OTHER PUBLICATIONS

Y. H. Yang and J. R. Abelson, J. Vac. Sci, Technol. A 13 (1995) 1145.

G.E. Jellison Jr., Thin Solid Films 234 (1993) 416.

J.-Th Zettler, Th. Trepk, L. Spanos, Y.-Z. Hu, and W. Richter, Thin Solid Films 234 (1993) 402.

* cited by examiner

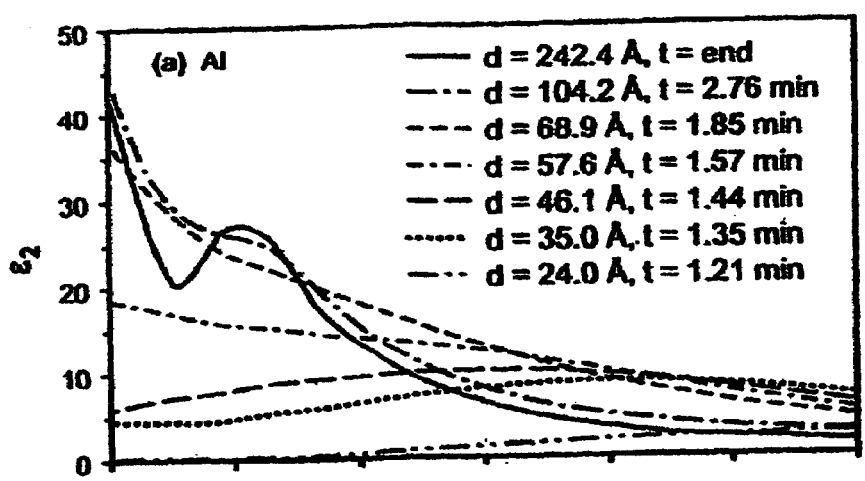
FIG. 5a1
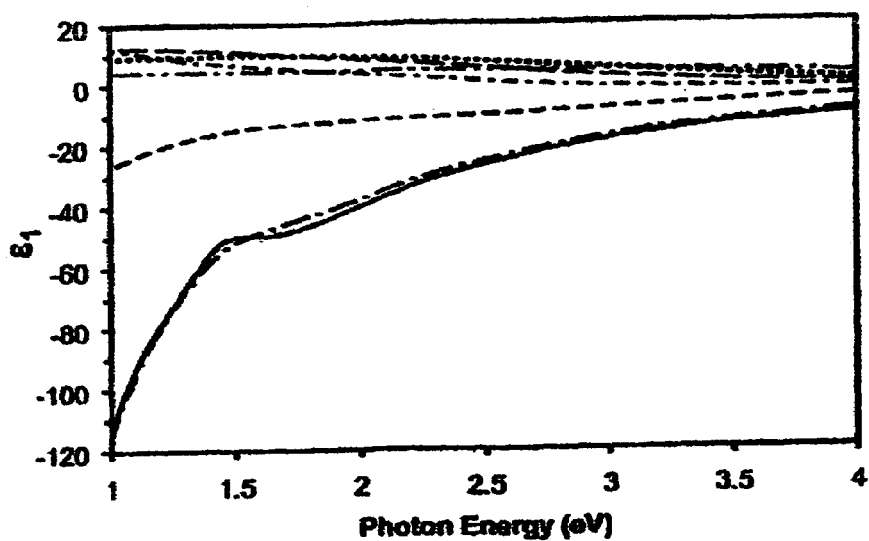
FIG. 5a2

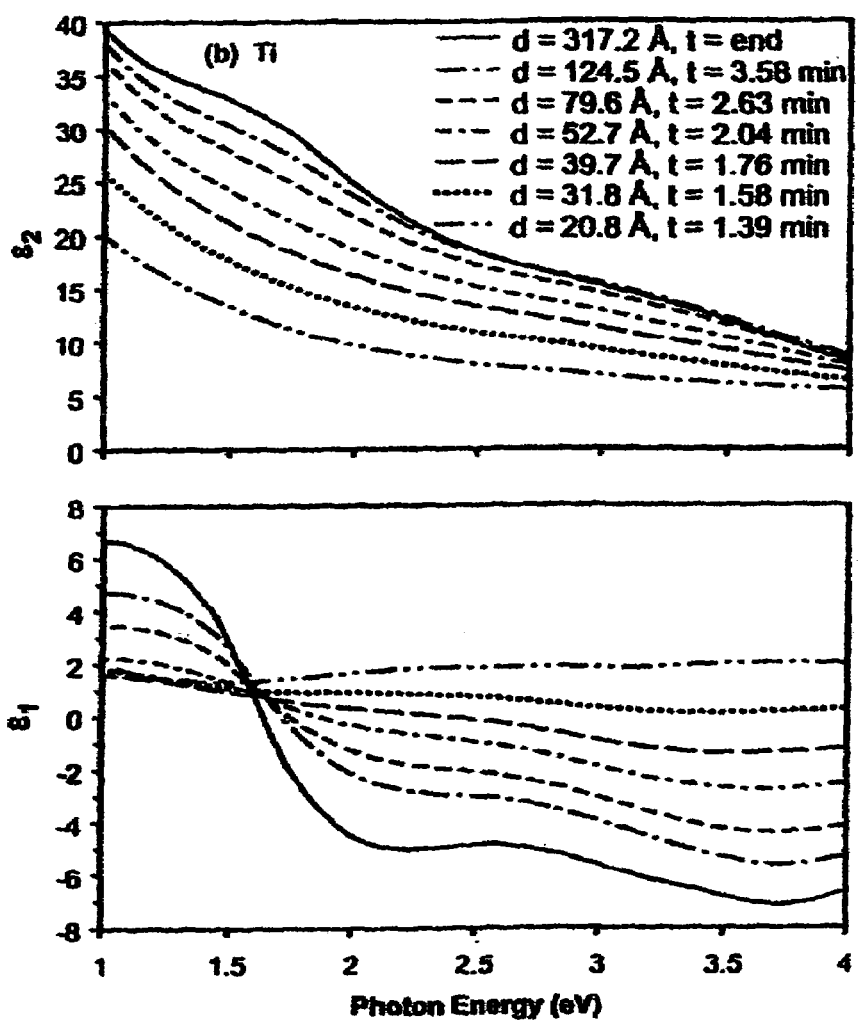
FIG. 5b1
FIG. 5b2

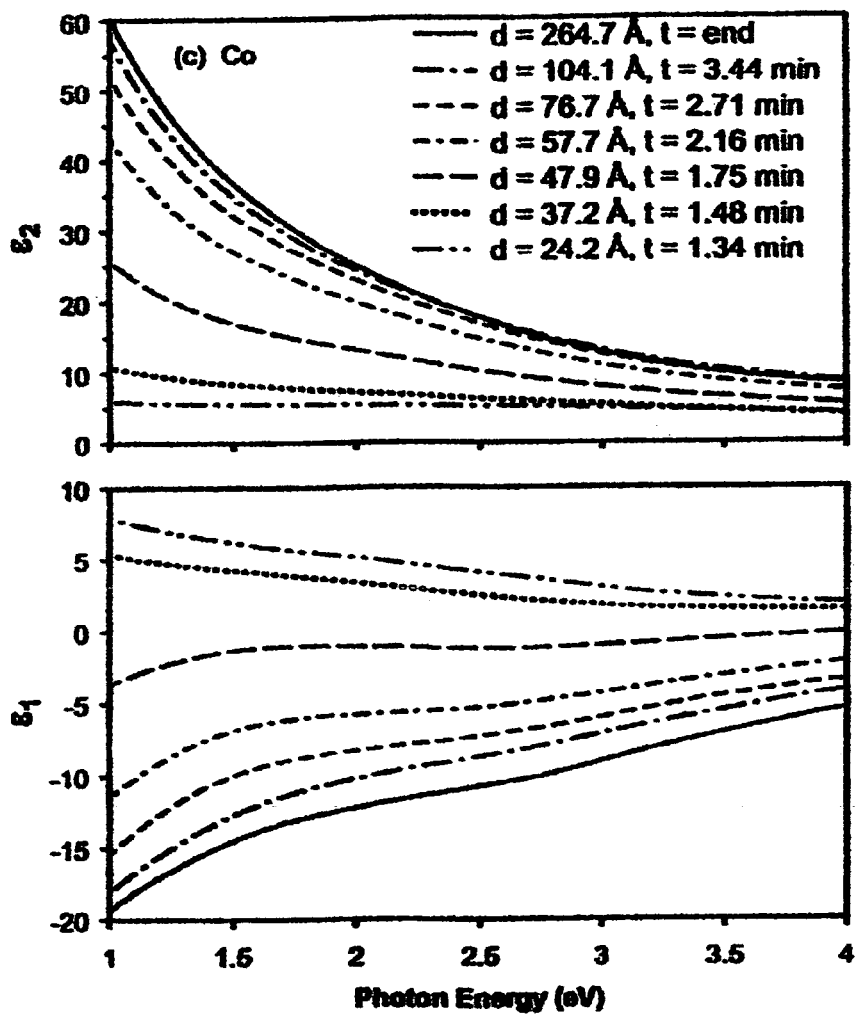
FIG. 5c1
FIG. 5c2

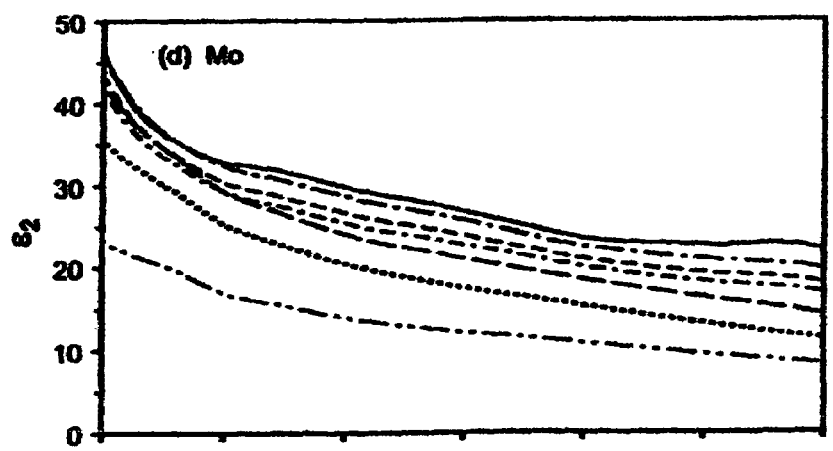
FIG. 5d1
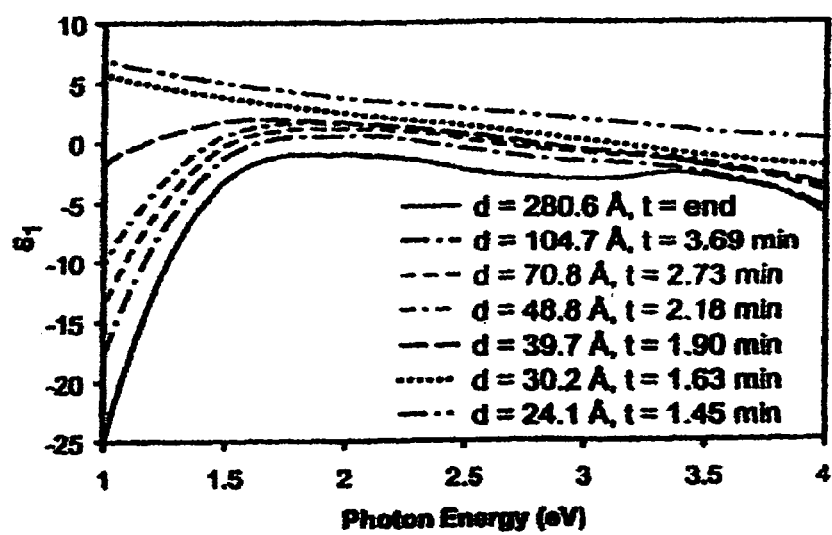
FIG. 5d2

DIELECTRIC FUNCTION OF THIN METAL FILMS DETERMINED BY COMBINED TRANSMISSION SPECTROSCOPIC ELLIPSOMETRY AND INTENSITY MEASUREMENTS

This Application Claims Benefit of Provisional Application Ser. No. 60/485,007 Filed Jul. 5, 2003.

TECHNICAL FIELD

The disclosed invention realtes to determination of thin film dielectric function and layer thicknesses, and more particularly to said determination using simultaneous in-situ transmission spectroscopic ellipsometric (SE) and transmission intensity (T) measurements to break correlation between thickness and optical constants of very thin absorbing metal films.

BACKGROUND

Accurate determination of the dielectric function of thin metal films (eg. <10 nm) by ex-situ measurements is difficult, because of the discontinuous nature of thereof, and rapid oxidization upon exposure to air. While in-situ ellipsometric measurements during film deposition can avoid this complication, correlation effects complicate unique determination of film thickness and dielectric function from ellipsometric data alone [1]. While utilization of reflection Spectroscopic Ellipsometry SE data in combination with reflection Intensity (I) data has been reported as an approach to overcome the problem, a need remains for a method of determining both dielectric function and film thickness in-situ.

With the present invention in mind a Search for relevant references was conducted. The following were identified:
1. An article by McGahan et al., Thin Solid Films 234 (1993) describes correlation effects which complicate determining both dielectric function and film thickness from ellipsometic data alone.
2. An Article by An et al, Rev. Sci. Instrum. 65 (1994) described utilizing reflection SE data in combination with reflection Intensity data.
3. H. Arwin and D. E. Aspnes, Thin Solid Films 113 (1984) 101 describes use of a strong feature in the substrate dielectric function, (e.g., the Si critical point structure near 3.4 eV.
4. H. V. Nguyen, Ilsin An, and R. W. Collins, Phys. Rev. Lett. 68 (1992) 994 describes the presence of plasmon-polariton band near 3.4 eV for the 35 Å Al film, in agreement with previous reported work.
5. H. V. Nguyen, Ilsin An, and R. W. Collins, Phys. Rev. B 47 (1993) 3947 describes transition from non-metallic to metallic behavior.
6. M2000XI, J. A. Woollam Co., Inc., Lincoln, Nebr. describes a Rotating Compensator Ellipsometer system as used to obtain results reported in theis Specification.
7. B. Johs, J. Hale, N. J. Ianno, C. M. Herzinger, T. Tiwald, and J. A. Woollam, Proc. SPIE 4449 (2001) 41 describes a dual spectrograph detector system, (with Si CCD and InGaAs photodiode detector arrays).
8. R. Kleim, L. Kuntzler, and A. El Ghemmaz, J. Opt. Soc. Am. A 11 (1994) 2550 describes use of aone averaged measurements were performed to minimize systematic errors in the data.
9. B. Johs and C. Herzinger, U.S. Pat. No. 6,034,777, 7 Mar. 2000 describes compensation of window birefingence was characterized and corrected for by performing a calibration (to determine the "out-of-plane" window effects) and a model fit to data acquired on the fused silica substrates before deposition (to determine the "in-plane" window effects)
10. P. I. Rovira and R. W. Collins, J. Appl. Phys. 85 (1999) 2015 describes previously reported work in which reflection intensity data was simultaneously acquired by a spectroscopic ellipsometer system utilized the DC signal component to extract the intensity information.

The following references 11, 12 and 13 describe calculating modulation ellipsometer parameters N, C, and S:

$$N=\cos 2\Psi, C=\sin 2\Psi \cos \Delta, S=\sin 2\Psi \sin \Delta$$

to account for the substrate induced depolarization:
11. R. Joerger, K. Forcht, A, Gombert, M. Khl, and W. Graf, Appl. Opt. 36 (1997) 319.
12. Y. H. Yang and J. R. Abelson, J. Vac. Sci, Technol. A 13 (1995) 1145.
13. G. E. Jellison Jr., Thin Solid Films 234 (1993) 416 which also describes weighting ellipsometric data according to their estimated error bars.
14. J.-Th Zettler, Th. Trepk, L. Spanos, Y.-Z. Hu, and W. Richter, Thin Solid Films 234 (1993) 402 describes use of cubic splines to parameterize a dielectric function.
15. Johs, French, Kalk, McGahan and Woollam, SPIE Vol. 2253, (1994) describes simultaneous use of reflection ellipsometry and transmission intensity signals to investigate multilayer structures.
16. Liphardt et al., U.S. Pat. No. 6,456,375, Issued Sep. 24, 2002 is disclosed to show it is known to take Transmission Data in ellipsometry.
17. Johs et al., U.S. Pat. No. 6,353,477, Issued Mar. 5, 2002 is disclosed as it identifies using A.C. (or (D.C. or comninations of A.C. and D.C.) components of electromagnetic beams in normalization.

The references are numbered as the relevance each is better identified throughout this Specification by reference thereto.

DISCLOSURE OF THE INVENTION

The present invention methodology provides that in-situ spectroscopic ellipsometric (SE) transmission data be combined with in-situ transmission intensity (T) data to unambiguously extract the metal film thickness and dielectric function throughout a film deposition procedure. Experimental work was conducted simultaneously acquiring SE and T data using a standard rotating compensator ellipsometer (RCE) system.

Metal films of Al, Co, Mo, and Ti were sputter-deposited at various deposition rates onto fused silica substrates at room temperature. The SE+T data are acquired by a rotating compensator ellipsometer (RCE), using only the AC signal components. Experimental results from the deposition of Al, Co, Mo, and Ti thin films on fused silica substrates are presented. The growing films were analyzed using the real-time acquired data. The dielectric function of Al changed most dramatically as a function of film thickness, while the Ti dielectric function exhibited the least changes.

The measurement beam angle of incidence was 65 degrees. Further, the present invention transmission intensity information was derived from the AC signal components of the RCE system. In situ SE+T results are reported for one film of each metal. The four reported films were chosen to have similar growth rates (about ($\approx$0.8 Å/s). It is well known that the optical properties of ultrathin metal films differ from those of bulk metal. This was most dramatically observed for the Al film. Model simulations assuming a constant bulk dielectric function deviate strongly from the experimental data during the initial film growth (nucleation and coalescence). The experimental SE+T data were fit much better with a 3-phase (substrate/film/ambient) model in which the film thickness and dielectric function were fit vs. time. A dramatic transition from non-metallic to metallic behavior, which can not be described by simple effective medium approximation models (i.e., film voids or surface roughness), is in good agreement with previous work [4,5]. The thickness dependence of the dielectric function for the other metals, while smaller compared to Al, is also presented. The main disadvantage of the present method is that transparent substrates are necessary, and the measurement is not possible after the absorbing film becomes optically thick.

A present invention method of determining dielectric function and layer thicknesses of a thin metal film deposited onto a substrate using simultaneous in-situ transmission spectroscopic ellipsometric (SE) and transmission intensity (T) measurements to break correlation between thickness and optical constants of very thin absorbing films, comprises the steps of: practicing steps a, b and c, said steps a, b and c being:

a) providing a system for depositing metal onto a substrate and a substrate;

b) providing a system for directing electromagnetic radiation toward said substrate at an oblique angle of incidence;

c) proposing a mathematical model for said substrate as metal is deposited thereonto which comprises at least dielectric function defining parameters and thickness;

d) during deposition of metal onto said substrate monitoring ellipsometric and intensity characterizing electromagnetic radiation which transmits through said substrate and enters a detector;

e) performing a plurality of time sequenced mathematical regressions to evaluate said dielectric function defining parameters and thickness using the detector output for both received ellipsometric and intensity characterizing electromagnetic radiation.

The oblique angle of incidence is preferably about 65 degrees.

The mathematical model comprises substrate, film and ambient and the thin film optical constants can be:
  held static for all regressions at a value first determined at the end of the thin film deposition are held constatn, and with said thin film growth then being analyzed backwards in time, with current thickness values seeding the next earliest; or
  fit at each regression, with the optical constants and thickness first determined at the end of the thin film deposition, and with said thin film growth then being analyzed backwards in time, with current values of optical constants and thickness seeding the next earliest.

Said method preferably provides that both ellipsometric and intensity data are acquired using only the AC signal components.

Finally, while a Rotating Compensator Ellipsometer was used in the experimental work reported in this Specification, and functional system for providing ellipsometric and intensity data can be used in the methodology, such as any ellipsometer selected from the group consisting of:
  rotating polarizer;
  rotating analyzer;
  rotating compensator;
  modulation element.

The dislosed invnetion will be better understood by reference to the Detailed Description Section of this Specification, in conjunction with the Drawings.

BRIEF DESCRIPTION OF THE DRAWINGS

FIGS. 5a1 and 5a2 shows evolution of thickness dependent effective dielectric function imaginary and ral parts determined by analysis of in-situ SE+T data for Al.

FIGS. 5b1 and 5b2 shows evolution of thickness dependent effective dielectric function imaginary and ral parts determined by analysis of in-situ SE+T data for Ti.

FIGS. 5c1 and 5c2 shows evolution of thickness dependent effective dielectric function imaginary and ral parts determined by analysis of in-situ SE+T data for Co.

FIGS. 5d1 and 5d2 shows evolution of thickness dependent effective dielectric function imaginary and ral parts determined by analysis of in-situ SE+T data for Mo films.

DETAILED DESCRIPTION

Figure 1:
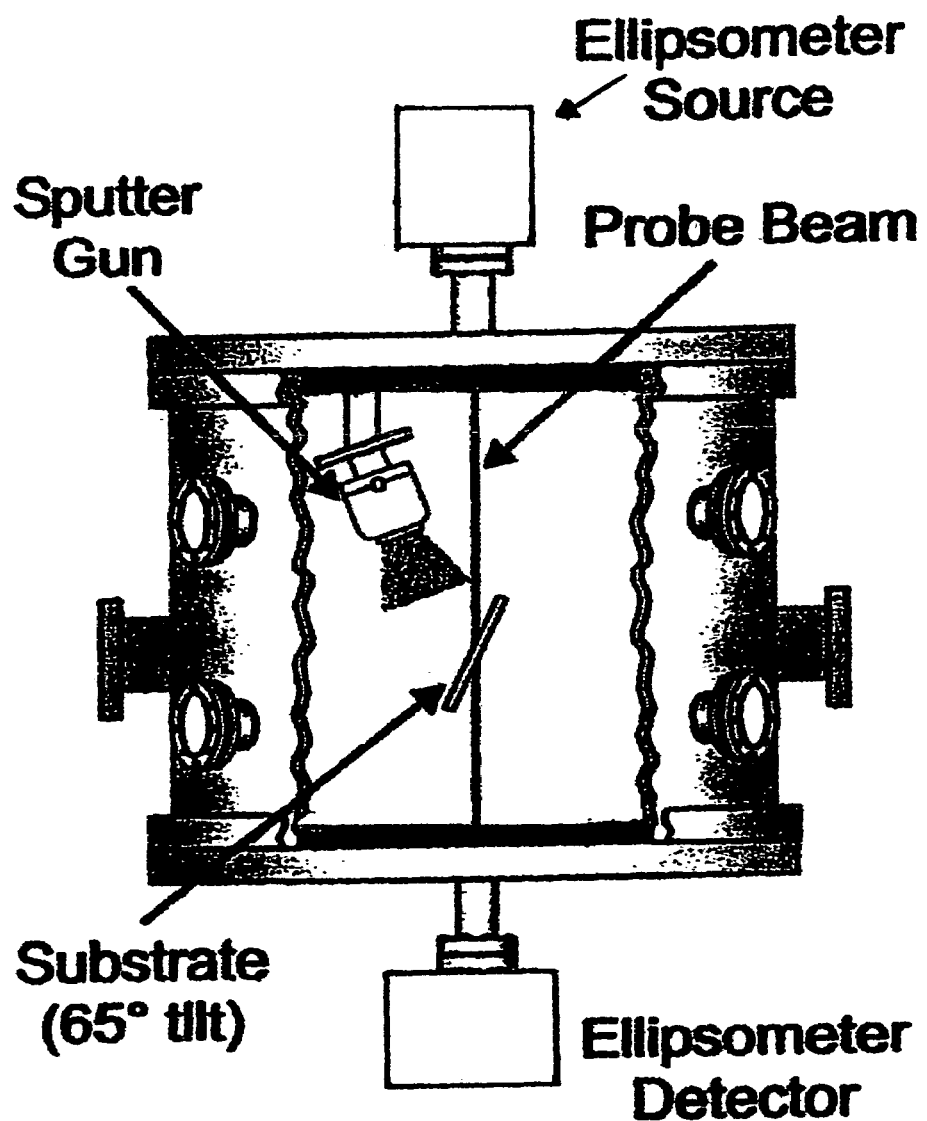
FIG. 1 shows a schematic of the experimental setup used in obtaining data.

Turning now to the Drawings, the experimental configuration used to obtain data reported herein is shown in FIG. 1. The deposition system is based on a magnetron sputtering gun where the input gas is injected between the anode and cathode gap. The sputtering gun is tilted approximately 20 degrees from vertical. Gas flow is controlled by an electronic mass flow control system, where argon is used as the sputter gas with a flow rate of 30 sccm. Pure metal sputter targets were used, with a diameter of 54 mm. The target power supply was set to constant DC current mode for all depositions. The system is evacuated by a turbo pump to a base pressure of about $1.3 \times 10^{-5}$ Pa. The pressure during deposition was typically 0.13 Pa. Fused silica substrates (3.2 mm thick) were used to allow in-situ transmission measurements. A substrate optical model, using book value SiO2 optical constants for the substrate with a about 4 SiO surface layer, was developed for the fused silica substrates based on ex-situ SE measurements. Window ports located on top and bottom of the chamber provided optical access to the substrate. A commercial rotating compensator ellipsometer (RCE) system [6] was mounted to the window ports. The substrate was tilted approximately 65 degrees towards the target, allowing simultaneous transmission ellipsometry and intensity measurements at an approximately 65 degree angle of incidence. During deposition, the sputter gun was oriented approximately 45 degrees to substrate normal. The film growth was initiated (plasma ignited) 1–1.2 minutes after the ellipsometer began acquiring data.

Both in-situ transmission ellipsometric and intensity data were acquired using the RCE system. This instrument uses a Xe arc lamp source and dual spectrograph detector system 171 (with Si CCD and InGaAs photodiode detector arrays) to simultaneously acquire data at 670 wavelengths over a spectral range of 240–1650 nm. Due to limited signal intensity at the end of the deposition run (when the beam is transmitted through about 250 of metal), the spectral range was limited to 1–4 eV, (ie. 310–1240 nm), for data analysis. Zone averaged measurements were performed to minimize systematic errors in the data 181, and the total data acquisition time was about 2.7 seconds, which includes the time for moving the analyzer between +/−45 degrees. Window birefingence was characterized and corrected for by performing a calibration (to determine the "out-of-plane" window effects) and a model fit to data acquired on the fused silica substrates before deposition (to determine the "in-plane" window effects) [7,9]. The angle of incidence and SiO thickness were also determined from the model fit prior to each deposition.

Previously reported work [2,10] in which reflection intensity data was simultaneously acquired by a spectroscopic ellipsometer system utilized the DC signal component to extract the intensity information. In this work, the transmission intensity data is derived from the detected AC signal components alone. This avoids some common problems that arise when measuring the DC signal level, which is susceptible to offset drift and 1/f noise in the electronics, and is also sensitive to fluctuations in the ambient light level (which could change during processing, e.g. light emission from a plasma). A derivation of the AC approach to intensity measurement with a RCE system is presented next, using the notation of Kleim [8].

The time-dependent intensity detected by a RCE system is given in eqn. 1., in which Ts is the average of the p- and s-transmittances for the sample (eqn. 2), and $K_\lambda$ is dependent on the light intensity, detector sensitivity, and electronic gain (and therefore varies strongly with wavelength). The K factors are determined from an initial intensity measurement on the bare fused silica substrate before each deposition, for which the expected transmission intensity values TS can be calculated vs. wavelength using a model with reference optical constants. Assuming the Mueller matrix definition for an isotropic sample given in eqn. 2, the detected unnormalized AC Fourier coefficients are shown in eqn. 3. In eqn. 3, P and A are the polarizer and analyzer azimuthal angles, and $\delta_\lambda$ is the compensator retardance, which varies as a function of wavelength.

$$I = K_\lambda T_S(DC + a_2 \cos(2\omega t) + b_2 \sin(2\omega t) + a_4 \cos(4\omega t) + b_4 \sin(4\omega t)) \quad (1)$$

$$M_s = T_s \begin{bmatrix} 1 & -N & 0 & 0 \\ -N & 1 & 0 & 0 \\ 0 & 0 & C & S \\ 0 & 0 & -S & C \end{bmatrix}, T_s = \frac{t_p t_p^* + t_s t_s^*}{2} \quad (2a)$$

$$N = \cos 2\Psi, \ C = \sin 2\Psi \cos \Delta, \ S = \sin 2\Psi \sin \Delta \quad (2b)$$

$$a_2 = -\sin 2A \sin 2P \sin \delta_\lambda S, \ b_2 = \sin 2A \cos 2P \sin \delta_\lambda S \quad (3a)$$

$$a_4 = \frac{1 - \cos\delta_\lambda}{2}[\cos 2P(\cos 2A - N) - \sin 2P \sin 2A \cdot C] \quad (3b)$$

$$b_4 = \frac{1 - \cos\delta_\lambda}{2}[\sin 2P(\cos 2A - N) + \cos 2P \sin 2A \cdot C] \quad (3c)$$

Assuming an analyzer azimuth of +/−45 degrees, which is typically used for data acquisition, eqns. 3 can be squared and added, resulting in the detected AC signal magnitude MAC given in eqn. 4. If the AC signal magnitudes at the 2nd and 4th harmonics are appropriately transformed by expressions containing the compensator retardance (which is known a priori), the transmitted beam intensity TM can be directly measured as shown in eqn. 5.

$$M_{AC}^2 = a_2^2 + b_2^2 + a_4^2 + b_4^4 = (K_\lambda T_s)^2 \left( \sin\delta_\lambda^2 S^2 + \frac{(N^2 + C^2)(1 - \cos\delta_\lambda)^2}{4} \right) \quad (4)$$

$$T_{\Delta t} = \sqrt{\frac{a_2^2 + b_2^2}{\sin\delta_\lambda^2} + \frac{4(a_4^2 + b_4^2)}{(1 - \cos\delta_\lambda)^2}} = K_\lambda T_S \sqrt{N^2 + C^2 + S^2} = K_\lambda T_S p \quad (5)$$

For non-depolarizing samples, eqn. 5 is further simplified, as $N^2 + C^2 + S^2 = 1$. However, in this work, the detected beam is slightly depolarized by multiple reflections within the 3.2 mm substrate. The measured transmission intensity is now the product of the average p- and s- transmittances (TS) and the degree of polarization p. This value can be readily calculated by the analysis software, which must properly calculate N, C, and S anyway to account for the substrate induced depolarization [11, 12].

RESULTS

Figures 2A, 2B:
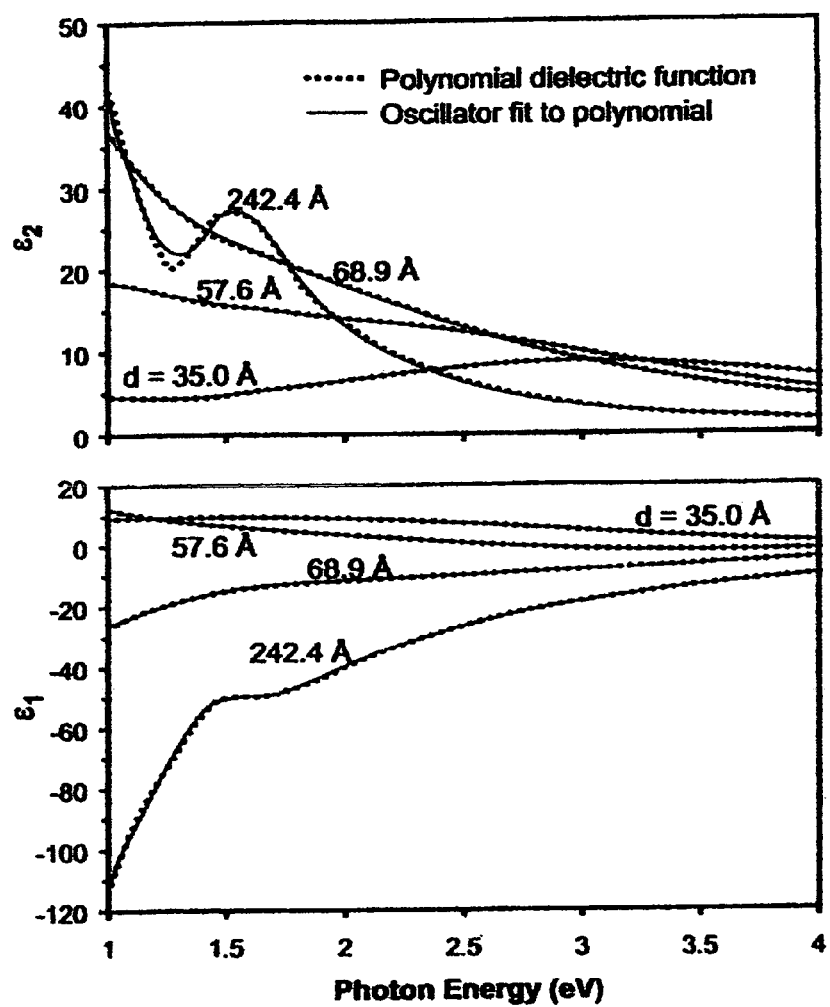
FIGS. 2a and 2b shows imaginary and real parts of an Al dielectric function at four thickness values obtained from polynomial model (dotted lines) of in-situ SE+T data. The polynomial dielectric function was fit to an oscillator model (solid lines) consisting of an ensemble of Lorentz oscillators to ensure K-K consistency.

The experimental SE+T data was fit using two models, both 3-phase (substrate/film/ambient). The first model used static optical constants determined from the bulk film growth regime. The second model allowed both the thickness and optical constants to fit at each time slice of SE+T data. The optical constants and thickness were first determined at the end of the deposition. The film growth was then analyzed backwards in time, with the current values seeding the next time slice. To extract the dielectric function and thickness, the experimental Ψ, Δ, and T data were combined in a regression analysis. In this analysis, the ellipsometric data points were properly weighted according to their estimated error bars [13], and the relative weight of the T data was empirically adjusted to achieve comparable SE and T data fits. The film dielectric function was modeled using piecewise continuous polynomial functions in $\epsilon_1$ and $\epsilon_2$ with defining points equally spaced in photon energy (a spacing of 0.2–0.4 eV was adequate to describe the structure in the dielectric function of these thin metal films). This polynomial approach is similar to previous work which used cubic splines to parameterize a dielectric function [14]. The most important advantage of the piecewise polynomial dispersion model is its flexibility to describe the changing dielectric function throughout film growth (nucleation, coalescence, and bulk) without assuming or imposing any dispersion model, and with a relatively small number of fit parameters (typically less than 20). However, the polynomial does not enforce the Kramers-Kronig (K-K) relationship. To ensure K-K consistency, the resulting polynomial dielectric functions at several Al film thickness values were fit to an oscillator model consisting of an ensemble of Lorentz oscillators. FIGS. 2a and 2b shows imaginary and real parts of an Al dielectric function at four thickness values obtained from polynomial model (dotted lines) of in-situ SE+T data. The polynomial dielectric function was fit to an oscillator model (solid lines) consisting of an ensemble of Lorentz oscillators to ensure K-K consistency fit to the polynomial dielectric function for the Al film at four thickness values during growth.

Figures 3A, 3B, 3C:
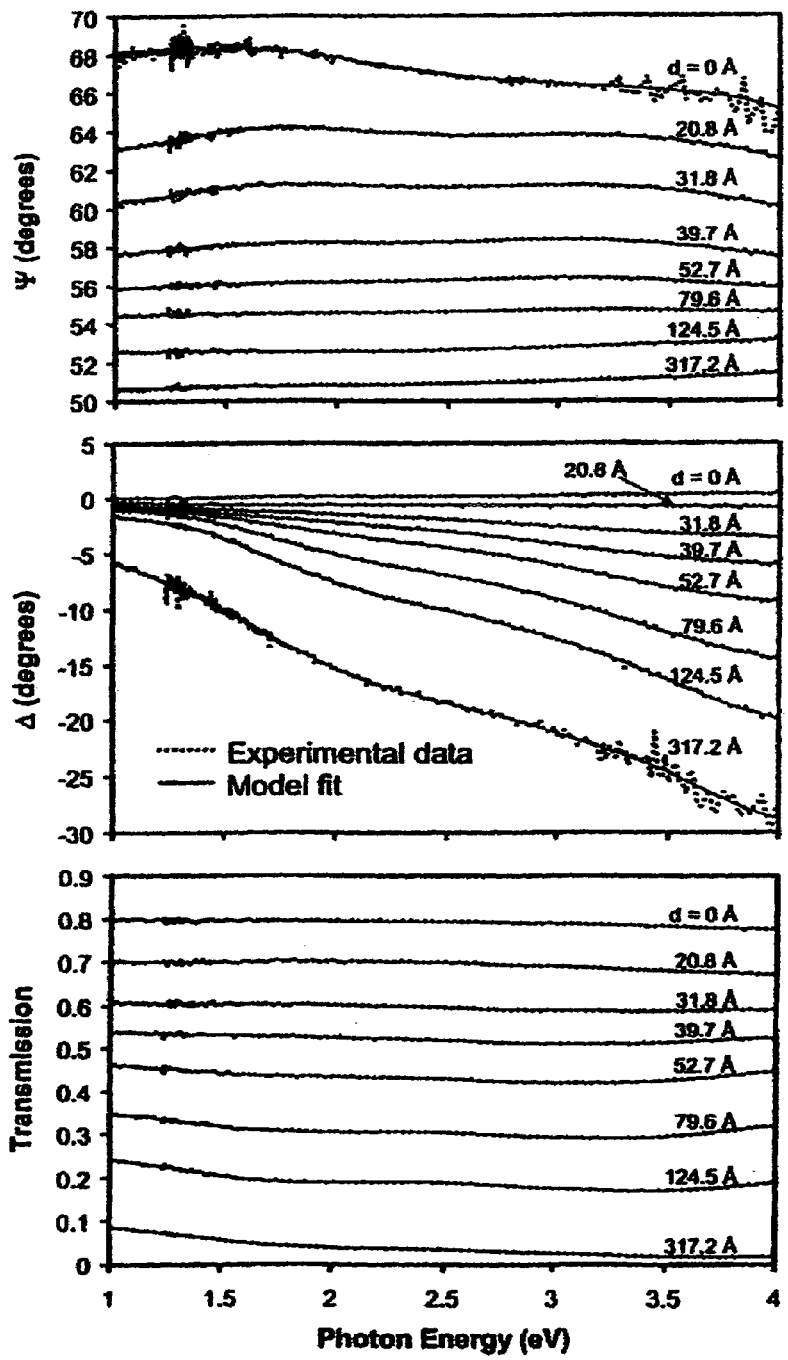
FIGS. 3a, 3b and 3c show PSI, DELTA and Transmission spectroscopic experimental data (dotted lines) and model fit (solid lines) for several Ti thickness values during growth.
Figure 4A:
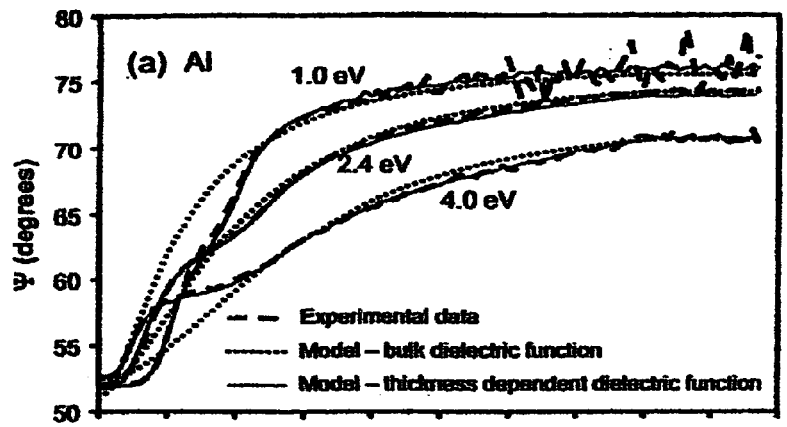
FIGS. 4a, 4b and 4c show dynamic experimental data at three energies for Al film growth. Model fits assuming bulk dielectric function (dotted lines) and thickness dependent dielectric function (solid lines).
Figure 4B:
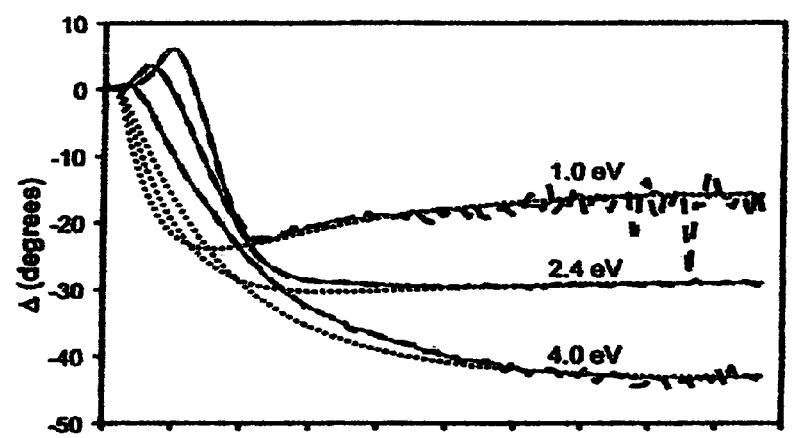
Figure 4C:
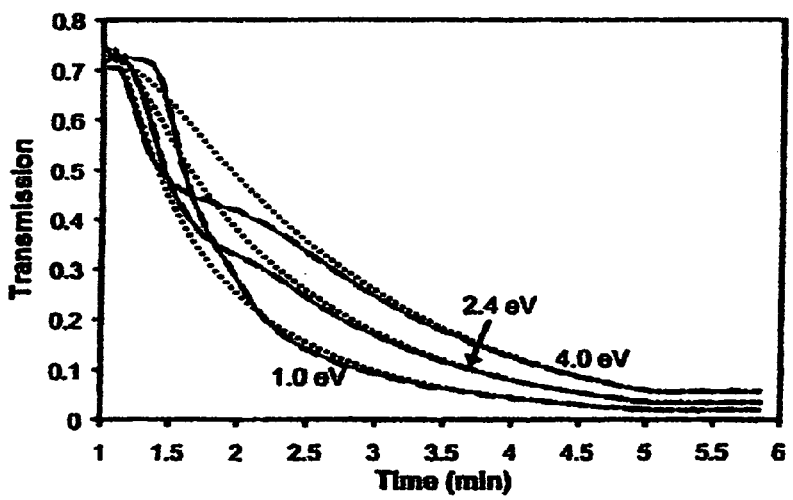
Figures 4D, 4E, 4F:
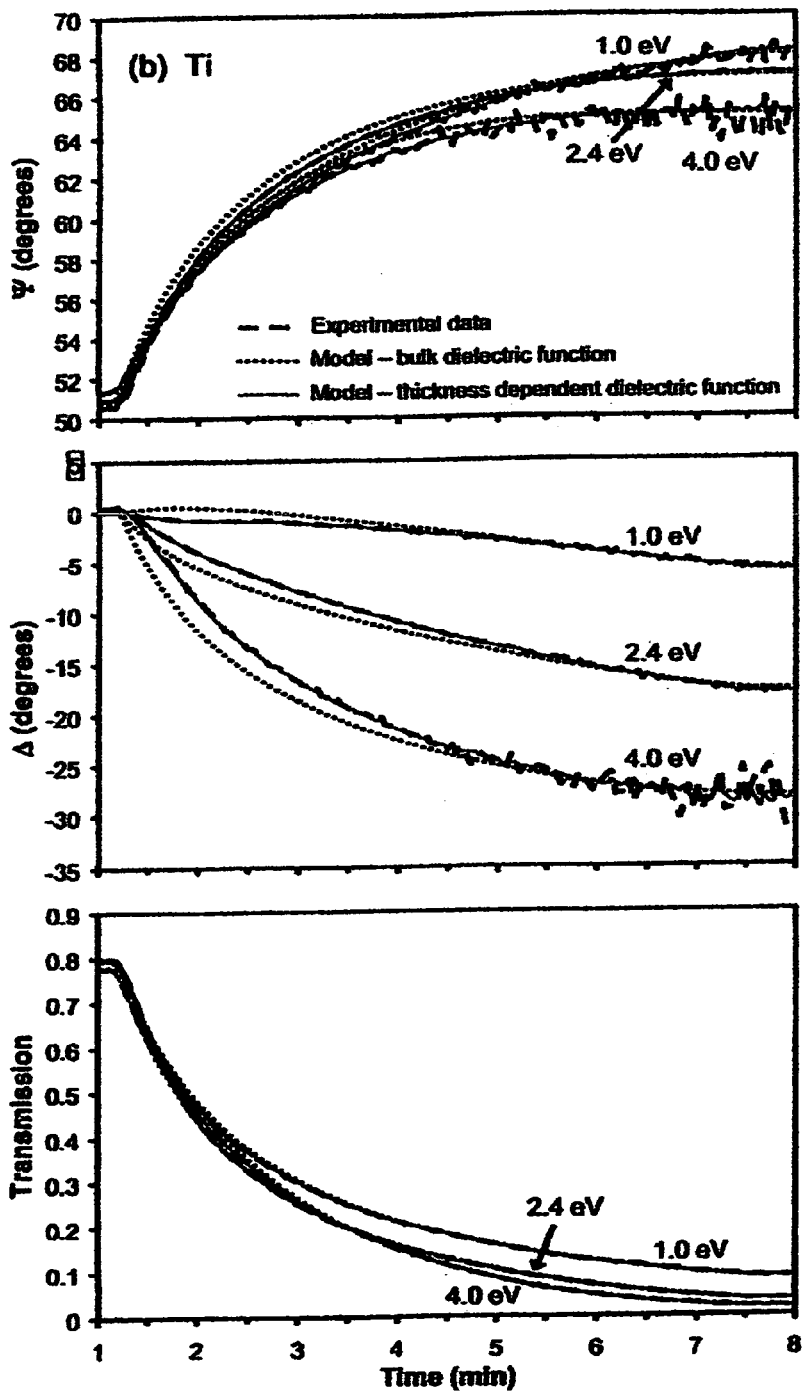
FIGS. 4d, 4e and 4f show dynamic experimental data at three energies for Ti film growth. Model fits assuming bulk dielectric function (dotted lines) and thickness dependent dielectric function (solid lines).

A typical example of the SE+T experimental data is shown in FIGS. 3a, 3b and 3c for the Ti film. Data are reported for the uncoated fused silica substrate as well as seven Ti thickness values. The polynomial model fit is also shown, which is in excellent agreement with the SE+T experimental data. The dynamic experimental data and fits are shown at three energies in FIGS. 4a, 4b and 4c show PSI and DELTA for the Al films and FIGS. 4d, 4e and 4f for the Ti films. From the raw data, it is evident that the initial film growth can not be described by bulk optical constants or by simple effective medium approximation models (i.e., film voids or surface roughness) since increases at the initiation of film growth. The Ψ and T data also show interesting features during the initial film growth. FIGS. 4a–4f show this behavior was most dramatic for the Al film and least dramatic for the Ti film. It is noted that Co and Mo were intermediate cases. In order to fit the data, it was necessary to vary the optical constants with thickness. The bulk optical constant model fit is more reasonable for the Ti film, but still deviates during initial film growth.

Figure 6:
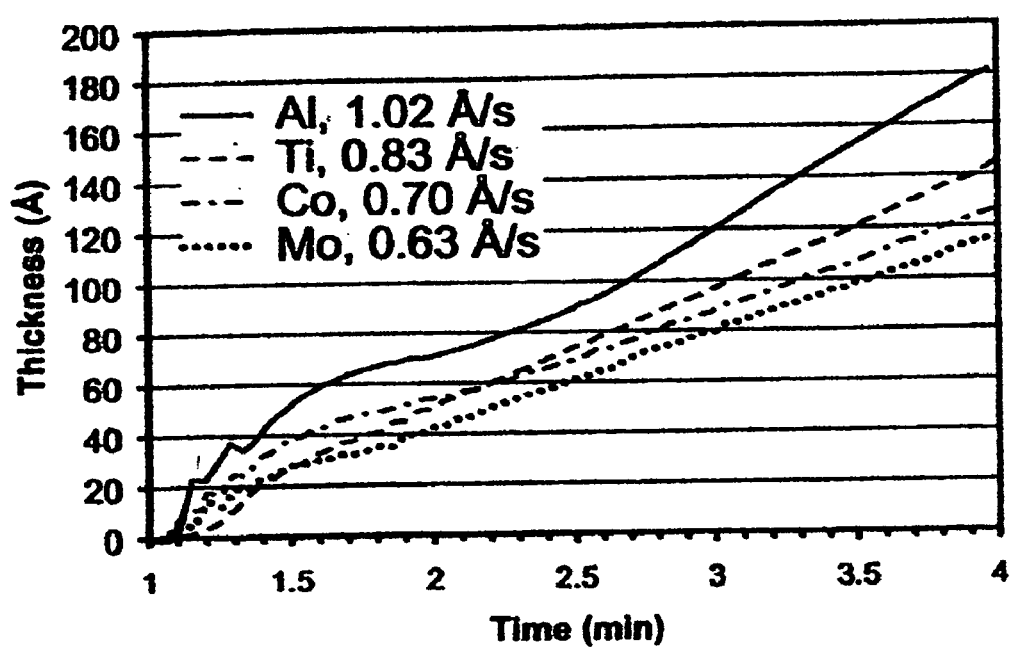
FIG. 6 shows effective thickness profile for first three minutes of growth for the four metal films. The plateau in thickness (most dramatic for Al) corresponds to the percolation threshold.

FIGS. 5a1 and 5a2 shows evolution of thickness dependent effective dielectric function imaginary and ral parts determined by analysis of in-situ SE+T data for Al. FIGS. 5b1 and 5b2 shows evolution of thickness dependent effective dielectric function imaginary and ral parts determined by analysis of in-situ SE+T data for Ti. FIGS. 5c1 and 5c2 shows evolution of thickness dependent effective dielectric function imaginary and ral parts determined by analysis of in-situ SE+T data for Co. FIGS. 5d1 and 5d2 shows evolution of thickness dependent effective dielectric function imaginary and ral parts determined by analysis of in-situ SE+T data for Mo films, (note the difference in scales in the various Figures). Features in the end-time dielectric functions are consistent with published values of the bulk metal optical constants. For the bulk Al film, the feature at 1.5 eV due to the (200) parallel-band transition dominates. This feature broadens and decreases as the thickness decreases, and vanishes before the percolation threshold is reached (metallic to non-metallic transition). A plasmon-polariton band develops near 3.4 eV for the 35 Al film, in agreement with previous reported work [4]. The determined dynamic thickness is shown in FIG. 6 for the first three minutes of film growth. A "knee" is observed in the effective thickness for all films, the most dramatic for the Al. The effective thickness increases rapidly at first due to the low density of the discontinuous film. The effective thickness plateaus as the film coalesces. After the percolation threshold, the effective thickness has an expected linear growth rate during bulk film growth. The plateau in the thickness corresponds to the change in effective dielectric function from non-metallic to metallic (abrupt decrease in 1 at low photon energies due to the Drude absorption). A similar trend is seen in the other metals. A rough estimate of the percolation threshold gives:

64 for the Al film,
47 for the Co film,
37 for the Mo film, and
20 for the Ti film.

It should be noted that surface roughness was not included in this analysis. Interpretation of a surface roughness value during the nucleation growth stage is not trivial since the dielectric function has substantial changes in this regime. For this reason, it was decided to report the effective dielectric function determined from analysis of the in-situ T+SE data. AFM measurements were made on all films to provide a measure of surface roughness. The AFM results are presented in Table 1.

TABLE 1

| Film | Gun Current (mA) | Growth Rate (Å/s) | Thickness (Å) | AFM Ra (nm) | AFM RMS (nm) |
| --- | --- | --- | --- | --- | --- |
| Al | 150 | 1.02 | 242.4 | 2.410 | 3.297 |
| Co | 200 | 0.70 | 264.7 | 1.069 | 1.365 |
| Mo | 100 | 0.63 | 280.6 | 1.147 | 1.414 |
| Ti | 400 | 0.83 | 317.2 | 1.346 | 1.799 |

The AFM picture for Al depicted grain sizes on the order of about 100 nm. No grain size information was evident from AFM pictures of the other metals (Co, No, and Ti).

In summary, In-situ spectroscopic ellipsometric transmission and transmission intensity were simultaneously measured to analyze the growth of Al, Co, Mo, and Ti metal films on fused silica substrates. Adding the third parameter, (ie. Intensity), to the SE data allows for unambiguous determination of the thickness and optical constants of the thin absorbing films. Both the SE and T data were simultaneously acquired using a rotating compensator ellipsometer. A thickness dependent dielectric function was necessary to model the experimental data, especially during the initial stages of film growth. The effective dielectric function was reported throughout growth for all metals studied. The Al dielectric function exhibited the most changes throughout growth, while the Ti dielectric function was the most stable.

Figure 7:
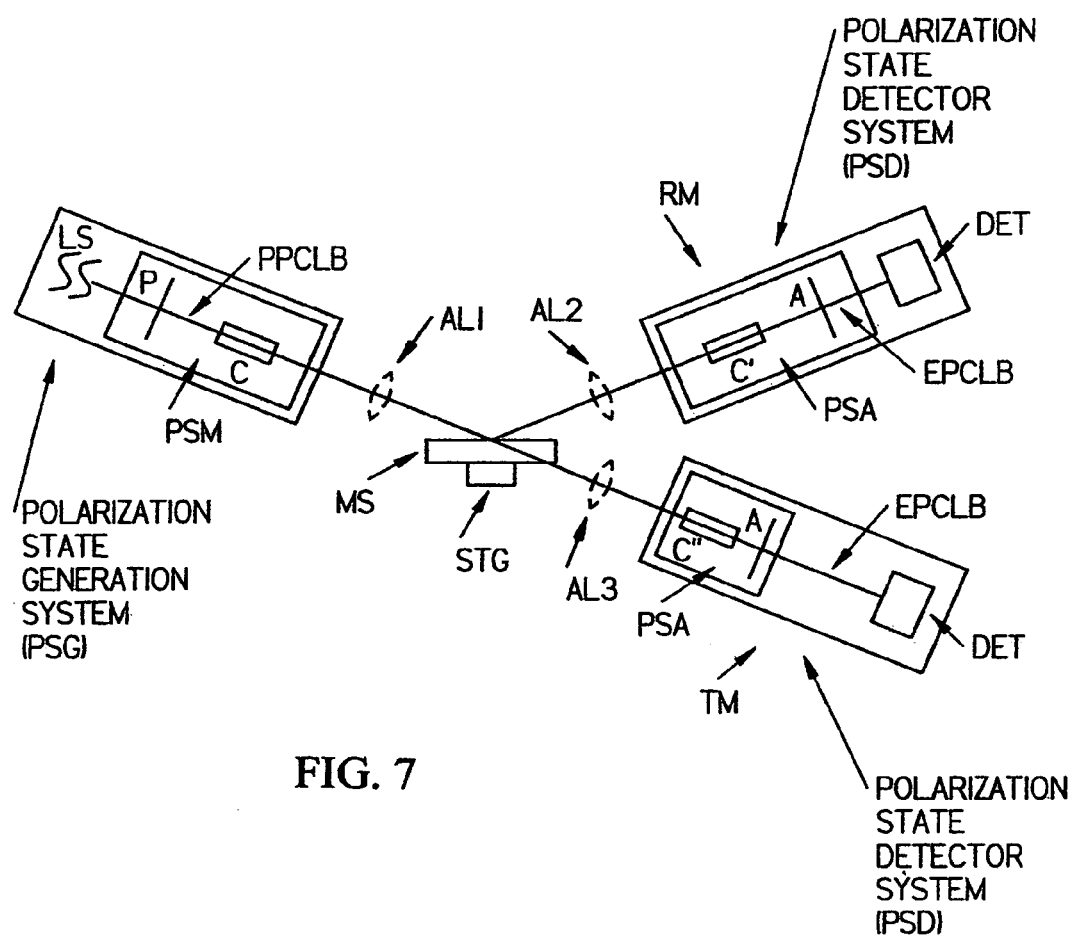
FIG. 7 provides insight to ellipsometer and polarimeter systems.

Finally, FIG. 7 is included to give better insight to ellipsometer and polarlmeter systems. Shown are that a Polarization State Generator (PSG) can comprise a Source of Electromagentic Radiation (LS), a Polarizer (P) and optionally a Compensator (C); and that a Polarization State Detector (PSD) can comprise a Detector (DET), Analyzer (A) and optionally a Compensator (C') (C"). Optional Lenses (AL1), (AL2) and (AL3) are also indicated. Note, both Reflection and Transmission configurations are shown. In operation, while taking data, at least one one element is usually caused to rotate. If it is the Polarizer, the system is a Rotating Polarizer Ellipsometer, if it is the Analyzer, the system is a Rotating Analyzer Ellipsometer, if it is a Compenator, the system is a Rotating Compensator Ellipsometer. An alternative interpretation provides that one of the Compensators (C) (C') (C") can be a Modulation element and the system is then a Modulation Element Ellipsometer. Further, during operation, electromagnetism polarization related elements, (eg. Polarizer (P) and Analyzer (A)) are typically not present during the acquiring of Intensity data.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A method of determining dielectric function and layer thicknesses of a thin metal film deposited onto a substrate using simultaneous in-situ transmission spectroscopic ellipsometric (SE) and transmission intensity (T) measurements to break correlation between thickness and optical constants of very thin absorbing films, comprising the steps of:
    practicing steps a, b and c, said steps a, b and c being:
        a) providing a system for depositing metal onto a substrate and a substrate;
        b) providing a system for directing electromagnetic radiation toward said substrate at an oblique angle of incidence;
        c) proposing a mathematical model for said substrate as metal is deposited thereonto which comprises at least dielectric function defining parameters and thickness;
        d) during deposition of metal onto said substrate monitoring ellipsometric and intensity characterizing electromagnetic radiation which transmits through said substrate and enters a detector;
        e) performing a plurality of time sequenced mathematical regressions to evaluate said dielectric function defining parameters and thickness using the detector output for both received ellipsometric and intensity characterizing electromagnetic radiation.

2. A method as in claim 1, in which the oblique angle of incidence is about 65 degrees.

3. A method as in claim 1, in which the oblique angle of incidence is between 10 and 65 degrees.

4. A method as in claim 1 in which the mathematical model comprises substrate, film and ambient and in which the thin film optical constants are determined once and held static for all following regressions.

5. A method as in claim 4 in which the thin film optical constants held constant are determined at the end of the thin film deposition, and with said thin film growth then being analyzed backwards in time, with current thickness values seeding the next earliest.

6. A method as in claim 1 in which the mathematical model comprises substrate, film and ambient and in which the thin film thickness and optical constants are fit at each regression, and with said thin film growth being analyzed backwards in time, with current values seeding the next earliest.

7. A method as in claim 1 in which the system for directing electromagnetic radiation toward said substrate at an oblique angle of incidence is a rotating compensator ellipsometer.

8. A method as in claim 1 in which the system for directing electromagnetic radiation toward said substrate at an oblique angle of incidence uses the same source of electromagnetism for both ellipsometry and intensity.

9. A method as in claim 1 in which ellipsometric and intensity data are acquired using only the AC signal components.

10. A method as in claim 1 in which ellipsometric and intensity data are acquired using using an ellipsometer system selected from the group consisting of:
    rotating polarizer;
    rotating analyzer;
    rotating compensator;
    modulation element.

11. A method of determining dielectric function and layer thicknesses of a thin metal film deposited onto a substrate using simultaneous in-situ transmission spectroscopic rotating compensator ellipsometric (SE) and transmission intensity (T) measurements to break correlation between thickness and optical constants of very thin absorbing films, comprising the steps of:
    practicing steps a, b and c, said steps a, b and c being:
        a) providing a system for vacuum depositing metal onto a substrate and a substrate;
        b) providing a rotating compensator system for directing electromagnetic radiation toward said substrate at an oblique angle of incidence of approximately 65 degrees;
        c) proposing a mathematical model for said substrate as metal is deposited thereonto which comprises at least dielectric function defining parameters and thickness;
        d) during deposition of metal onto said substrate monitoring AC components of ellipsometric and intensity characterizing electromagnetic radiation which transmits through said substrate and enters a detector;
        e) performing a plurality of time sequenced mathematical regressions to evaluate said dielectric function defining parameters and thickness using the detector output for both received ellipsometric and intensity characterizing electromagnetic radiation.

12. A method as in claim 11 in which the mathematical model comprises substrate, film and ambient and in which the thin film optical constants are are determined once and held static for all following regressions.

13. A method as in claim 12 in which the thin film optical constants held constant are determined at the end of the thin film deposition, and with said thin film growth then being analyzed backwards in time, with current thickness values seeding the next earliest.

14. A method as in claim 11 in which the mathematical model comprises substrate, film and ambient and in which the thin film thickness and optical constants are fit at each regression, and with said thin film growth being analyzed backwards in time, with current values seeding the next earliest.

15. A method as in claim 11 in which the system for directing electromagnetic radiation toward said substrate at an oblique angle of incidence uses the same source of electromagnetism for both ellipsometry and intensity.

* * * * *